US00PP24915P2

(12) United States Plant Patent
Allen

(10) Patent No.: US PP24,915 P2
(45) Date of Patent: Sep. 23, 2014

(54) ***LEUCANTHEMUM* PLANT NAMED 'SHAPCOTT GOSSAMER'**

(50) Latin Name: *Leucanthemum×superbum*
Varietal Denomination: Shapcott Gossamer

(71) Applicant: Anita Allen, South Molton (GB)

(72) Inventor: Anita Allen, South Molton (GB)

( * ) Notice: Subject to any disclaimer, the term of this patent is extended or adjusted under 35 U.S.C. 154(b) by 87 days.

(21) Appl. No.: 13/815,088

(22) Filed: Jan. 30, 2013

(51) Int. Cl.
*A01H 5/00* (2006.01)

(52) U.S. Cl.
USPC ..... Plt./285

(58) Field of Classification Search
CPC ..... A01H 5/00
USPC ..... Plt./285
See application file for complete search history.

*Primary Examiner* — Anne Grunberg
(74) *Attorney, Agent, or Firm* — Penny J. Aguirre

(57) ABSTRACT

A new cultivar of *Leucanthemum*, 'Shapcott Gossamer', characterized by its capitulums with fine ray florets that a gracefully pendulant, its cold hardiness to −20° C., its flower stems that stand erect and do not lodge, its height of about 76 cm, its dependably long-lived habit, its use as a long lived cut flower, and its deep green healthy foliage that has been observed to be disease free under the conditions tested.

2 Drawing Sheets

Botanical classification: *Leucanthemum×superbum.*
Variety denomination: 'Shapcott Gossamer'.

CROSS REFERENCE TO RELATED APPLICATIONS

This application is co-pending with a U.S. Plant Patent Application filed for a plant derived from the same breeding program that is entitled *Leucanthemum* Plant Named 'Shapcott Summer Clouds' (U.S. Plant patent application Ser. No. 13/815,089) and *Leucanthemum* Plant Named 'Shapcott Ruffles' (U.S. Plant patent application Ser. No. 13/815,086).

BACKGROUND OF THE INVENTION

The present invention relates to a new and distinct cultivar of *Leucanthemum×superbum* and will be referred to hereafter by its cultivar name, 'Shapcott Gossamer'. 'Shapcott Gossamer' represents a new Shasta daisy grown for landscape use and for use as a cut flower.

The new cultivar of *Leucanthemum* arose from an ongoing controlled breeding project by the Inventor in South Molton, Devon, United Kingdom. The new cultivar derived from crosses made in 1995 between unnamed proprietary plants in the Inventor's breeding program. Seeds were pooled from the crosses and the parents are unknown. The Inventor selected 'Shapcott Gossamer' as a single unique plant amongst the seedlings that resulted from the above crosses in 1998.

Asexual propagation of the new cultivar was first accomplished by division by the Inventor in 1998 in South Molton, Devon, United Kingdom. Asexual propagation by division has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Shapcott Gossamer' as a unique cultivar of *Leucanthemum.*

1. 'Shapcott Gossamer' exhibits capitulums with fine ray florets (15 mm in width) that a gracefully pendulant.
2. 'Shapcott Gossamer' exhibits cold hardiness to −20° C.
3. 'Shapcott Gossamer' reached a height of about 76 cm (25 feet).
4. 'Shapcott Gossamer' exhibits flower stems that stand erect and do not lodge.
5. 'Shapcott Gossamer' is dependably long-lived.
6. 'Shapcott Gossamer' exhibits deep green healthy foliage.
7. 'Shapcott Gossamer' has been observed to be disease free under the conditions tested.
8. 'Shapcott Gossamer' exhibits flowers that are long lived as a cut flower.

The new *Leucanthemum* can be most closely compared to the cultivars 'Phyllis Smith' (not patented) and 'Beauté Nivelloise' (not patented). They are both similar to 'Shapcott Gossamer' in having capitulums with fine florets. However, 'Phyllis Smith' differs from 'Shapcott Gossamer' in having ray florets that are not as fine, stiffer and not as pendulant, in being a slighter shorter in height, and in being a having a less vigorous growth habit. 'Beauté Nivelloise' differs from 'Shapcott Gossamer' in having smaller capitulums with ray florets that are not as fine, in having stems that tend to lodge, in being slightly shorter in height, in having lighter green leaves, and in being shorter lived with less cold hardiness. 'Shapcott Gossamer' can also be compared to the cultivars from the same breeding program; 'Shapcott Ruffles' and 'Shapcott Summer Clouds'. 'Shapcott Ruffles' differs from 'Shapcott Gossamer' in having capitulums with more ray florets that are wider and in being shorter in height. 'Shapcott Summer Clouds' differs from 'Shapcott Gossamer' in having capitulums with more ray florets that are wider and shorter, and more irregularly placed around the disk florets.

BRIEF DESCRIPTION OF THE DRAWINGS

The accompanying colored photographs illustrate the overall appearance and distinct characteristics of the new *Leucan-*

*themum*. The photographs were taken of plants about 2 years in age as grown in a garden in South Molton, Devon, United Kingdom.

Figure 1:
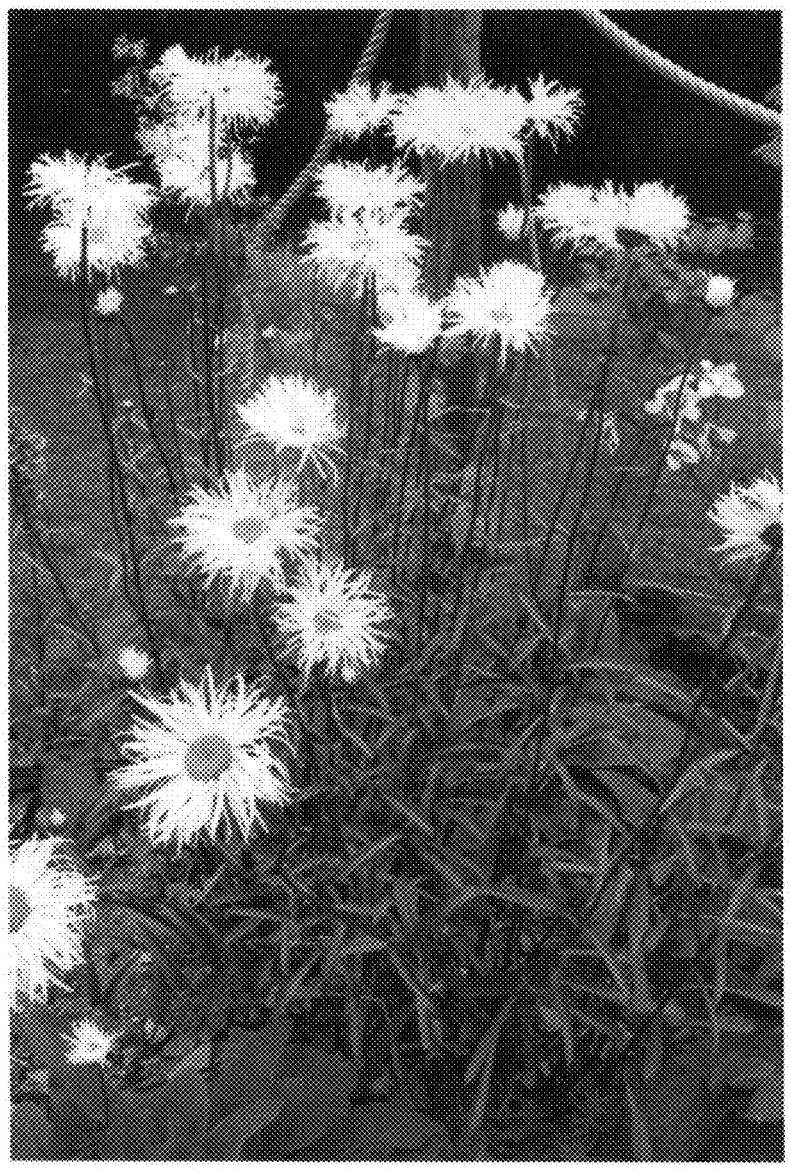

The photograph in FIG. 1 illustrates the plant habit of 'Shapcott Gossamer' in bloom.

Figure 2:
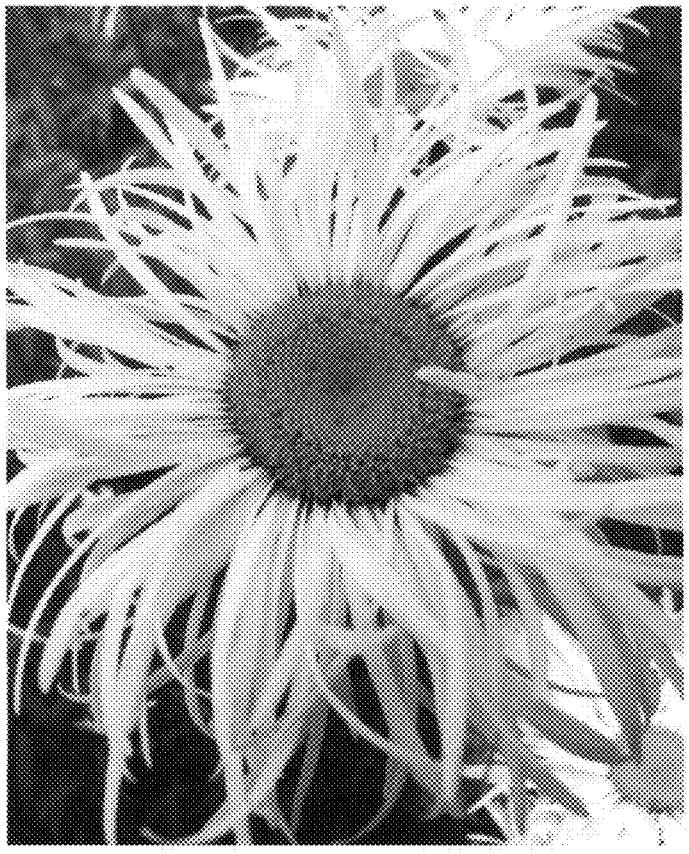

The photograph in FIG. 2 provides a close-up view of the capitulums of 'Shapcott Gossamer'.

Figure 3:
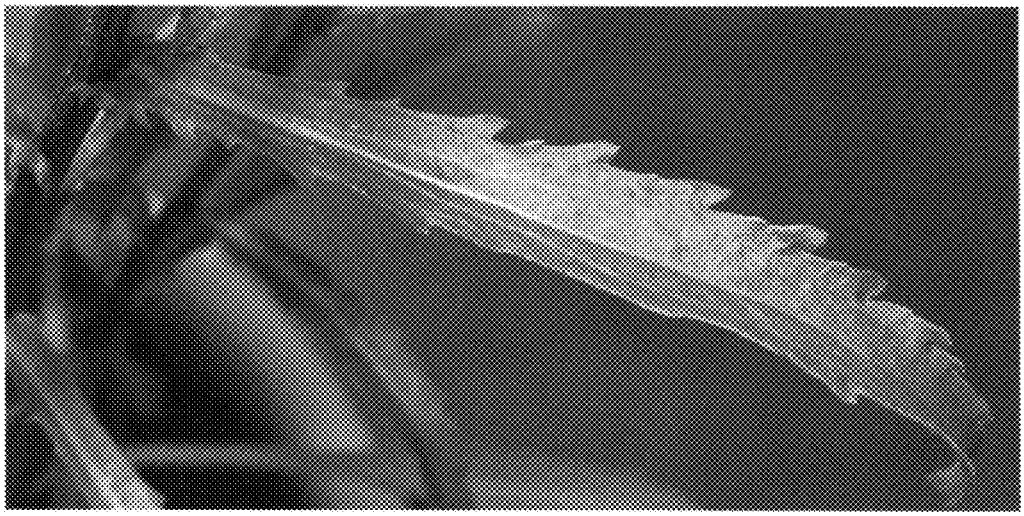

FIG. 3 provides a close-up view of a leaf of 'Shapcott Gossamer'. The colors in the photographs may differ slightly from the color values cited in the detailed botanical description, which accurately describe the colors of the new Leucanthemum.

BOTANICAL DESCRIPTION OF THE PLANT

The following is a detailed description of three month-old plants from a division of the new cultivar as grown outdoors in 5.9-liter containers in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms for 10 weeks from late June to early August in South Molton, Devon, United Kingdom.

*Plant type*.—Herbaceous perennial, long lived.

*Plant habit*.—Upright, freely branching.

*Height and spread*.—About 70 cm in height and 60 cm in width.

*Diseases*.—Has been observed to be disease free under the conditions tested.

*Cold hardiness*.—At least to −20° C.

*Root description*.—Fibrous roots, freely branched, dense.

*Growth rate*.—Vigorous.

*Propagation*.—Division.

Stem description:

*Stem shape*.—Rounded.

*Stem aspect*.—Primarily upright without a tendency to lodge.

*Stem strength*.—Very strong.

*Stem color*.—143A, axial ribs are 200A to 200B.

*Stem surface*.—Un-deep axial ribs, moderately glossy, sparsely covered in short strigose hairs average of 0.3 mm in length and 157D in color.

*Lateral branch size*.—Average of 45 cm in length and 9 mm in diameter.

*Quantity of lateral branches*.—About 3 lateral stems per main stem.

*Internode length*.—An average of 2.4 cm.

*Branching*.—Moderately branched.

Foliage description:

*Leaf division*.—Simple.

*Leaf shape*.—Oblanceolate.

*Leaf base*.—Cuneate, short decurrent.

*Leaf apex*.—Broadly acute.

*Leaf margin*.—Serrate.

*Leaf venation*.—Pinnate, upper surface 143B to 143C in color, lower surface 144A in color.

*Leaf attachment*.—Sessile.

*Leaf arrangement*.—Alternate.

*Leaf surface*.—Upper and lower surfaces; smooth and slightly glossy.

*Leaf color*.—Young foliage; upper surface N137B, lower surface 146A, mature foliage; upper surface N137B, lower surface between 146B and 147B.

*Leaf size*.—Average of 11.5 cm in length and 2.3 cm in width.

Inflorescence description:

*Type*.—Capitulum, heterogamous with fine ligulate ray florets around disk florets in the center, on borne terminals and axillary nodes of lateral branches.

*Capitulum number*.—Average 10 inflorescences per lateral stem and 30 per plant.

*Lastingness of inflorescence*.—About 3 weeks.

*Lastingness as a cut flower*.—About 7 days in water without additives.

*Capitulum size*.—Matures to about 6 cm in depth and 10.1 cm in diameter, disk size is about 2.5 cm in diameter, receptacle is 3 mm in height and 1.4 cm in diameter.

*Fragrance*.—None detected.

*Involucral bracts*.—About 50 arranged in 3 rows, about 9 mm in length and 3 mm in width, ovate in shape, broad acute apex, broad cuneate base, entire margin, smooth and dull on both surfaces, color; upper and lower surface; 143C, margins N199C.

*Buds*.—Globose in shape, an average of 9 mm in length and 1.3 cm in diameter, 144C in color.

*Peduncle*.—Terminal peduncle; 18.5 cm in length, very strong, slightly glossy, smooth, with un-deep axial ribs, 143C in color and held straight upright, fourth peduncle; 24.5 cm in length, very strong, slightly glossy, smooth, with un-deep axial ribs, 143C in color and held at an angle of 30°, seventh peduncle; 36.5 cm in length, very strong, slightly glossy, smooth, with un-deep axial ribs, 143C in color and held at an angle of 30°.

*Ray florets* (*sterile*).—Rotate, Average 50, arranged in multiple rows, three-parted in shape, very slightly upright an average angle of 20°, about 4.7 cm in length and 1.5 mm in width, acute apex on lobes, attenuate base, entire margin, smooth on both surfaces, color: upper side; when opening and fully opened; NN155D, lower surface; when opening and fully opened; NN155D.

*Disk florets* (*bisexual*).—Numerous, about 300, rotate in shape, acute apex, lower 60% fused into a short tube, about 5 mm in length, 1 mm in width at base, 1.5 mm at apex, color: immature; 145C, base 150B, mature apex; 13A, mature mid-section; 145B, mature base; 150B.

Reproductive organs (present on disk florets only):

*Gynoecium*.—Pistil; 1, 2.5 mm in length, style; 2 mm in length and 151D in color, ovary is 151D in color.

*Androcoecium*.—Stamens; 5, fused, form a cylinder around style, about 3 mm in length, anther; basifixed and linear in shape, 2 mm in length and 151C in color, pollen; low and 13A in color.

*Fruit/seed*.—None observed.

It is claimed:

1. A new and distinct cultivar of *Leucanthemum* plant named 'Shapcott Gossamer' substantially as herein illustrated and described.

* * * * *